(12) United States Patent
Wong et al.

(10) Patent No.: US 7,760,082 B2
(45) Date of Patent: Jul. 20, 2010

(54) SYSTEM AND METHOD FOR ACTIVE MONITORING AND DIAGNOSTICS OF LIFE SIGNS USING HEARTBEAT WAVEFORM AND BODY TEMPERATURE REMOTELY GIVING THE USER FREEDOM TO MOVE WITHIN ITS VICINITY WITHOUT WIRES ATTACHMENT, GEL, OR ADHESIVES

(76) Inventors: Chon Meng Wong, 34 Mark Dr., Lincoln, RI (US) 02865; An-Kwok Ian Wong, 34 Mark Dr., Lincoln, RI (US) 02865; Belinda T. Wong, 34 Mark Dr., Lincoln, RI (US) 02865

( * ) Notice: Subject to any disclaimer, the term of this patent is extended or adjusted under 35 U.S.C. 154(b) by 281 days.

(21) Appl. No.: 11/523,577

(22) Filed: Sep. 20, 2006

(65) Prior Publication Data
US 2007/0152812 A1    Jul. 5, 2007

Related U.S. Application Data

(60) Provisional application No. 60/718,723, filed on Sep. 21, 2005.

(51) Int. Cl.
*G08B 1/08* (2006.01)
*A61B 5/02* (2006.01)
*A61B 7/00* (2006.01)

(52) U.S. Cl. .................. 340/539.12; 600/508; 600/528; 600/586

(58) Field of Classification Search ............ 340/539.12; 600/508–528, 481–507, 586, 300–301, 552, 600/529–543, 549
See application file for complete search history.

(56) References Cited

U.S. PATENT DOCUMENTS

| | | | |
|---|---|---|---|
| 3,247,324 A | 4/1966 | Cefaly et al. | |
| 4,509,527 A * | 4/1985 | Fraden | 600/484 |
| 4,528,690 A | 7/1985 | Sedgwick | |
| 4,781,200 A | 11/1988 | Baker | |
| 5,140,992 A * | 8/1992 | Zuckerwar et al. | 600/528 |
| 5,365,937 A | 11/1994 | Reeves et al. | |
| 5,471,880 A | 12/1995 | Lang et al. | |
| 5,515,865 A | 5/1996 | Scanlon | |

(Continued)

OTHER PUBLICATIONS

International Search Report of PCT/US06/36751.

*Primary Examiner*—Benjamin C Lee
*Assistant Examiner*—Michael Shannon
(74) *Attorney, Agent, or Firm*—Steptoe & Johnson LLP

(57) ABSTRACT

A system and method that uses non-invasive method, such as a wearable module equipped with sensors placed on a subject connected to a computer-linked module, to monitor life signs like heartbeat waveforms, body temperatures, indicating the health of a living being or a dynamic system. The health of the system is defined by a set of known good spectra with deviations triggering alerts. A garment embedded with a piezoelectric material and a temperature sensor, when placed in contact with the body, captures acoustic waves from the heart and body temperature. Both sensors are connected to a garment-mounted module with a flexible printed antenna. Another module with reconfigured daughterboard software forms a bidirectional wireless data connection to a computer. A software program compares the received spectrum to its database spectrum based on a set of rules and alerts the user when it deviates.

32 Claims, 16 Drawing Sheets

U.S. PATENT DOCUMENTS

| | | | |
|---|---|---|---|
| 5,595,188 A * | 1/1997 | Kassal | 600/586 |
| 5,684,460 A | 11/1997 | Scanlon | |
| 5,795,300 A * | 8/1998 | Bryars | 600/500 |
| 5,812,678 A | 9/1998 | Scalise et al. | |
| 5,827,198 A | 10/1998 | Kassal | |
| 5,840,039 A | 11/1998 | Heikkila | |
| 5,853,005 A | 12/1998 | Scanlon | |
| 5,871,499 A * | 2/1999 | Hahn et al. | 606/202 |
| 5,885,222 A | 3/1999 | Kassal et al. | |
| 6,053,872 A | 4/2000 | Mohler | |
| 6,238,338 B1 | 5/2001 | DeLuca et al. | |
| 6,285,899 B1 | 9/2001 | Ghaem et al. | |
| 6,341,229 B1 | 1/2002 | Akiva | |
| 6,575,916 B2 | 6/2003 | Halleck et al. | |
| 6,579,231 B1 * | 6/2003 | Phipps | 600/300 |
| 6,616,606 B1 | 9/2003 | Petersen et al. | |
| 6,675,041 B2 | 1/2004 | Dickinson | |
| 6,781,284 B1 | 8/2004 | Pelrine et al. | |
| 6,897,788 B2 | 5/2005 | Khair et al. | |
| 2002/0173828 A1 * | 11/2002 | Gozani et al. | 607/48 |
| 2005/0004460 A1 * | 1/2005 | Taylor et al. | 600/437 |
| 2005/0116820 A1 * | 6/2005 | Goldreich | 340/539.12 |
| 2005/0194012 A1 | 9/2005 | Ito et al. | |
| 2006/0122675 A1 * | 6/2006 | Libbus et al. | 607/116 |
| 2007/0293781 A1 * | 12/2007 | Sims et al. | 600/534 |

\* cited by examiner

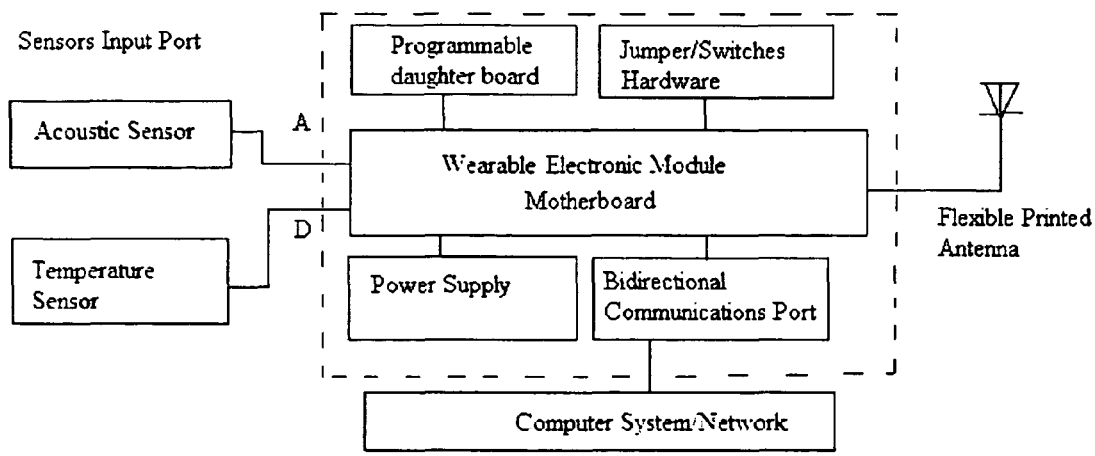
Figure 1. Architecture of the Life Sign Active Monitoring and Diagnostic System
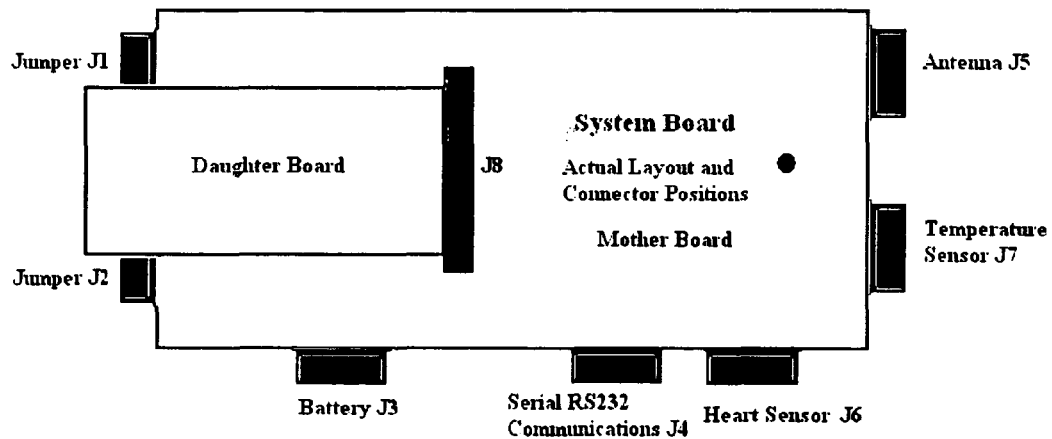
Figure 2. The WEM unit with motherboard and daughter board and the various connectors

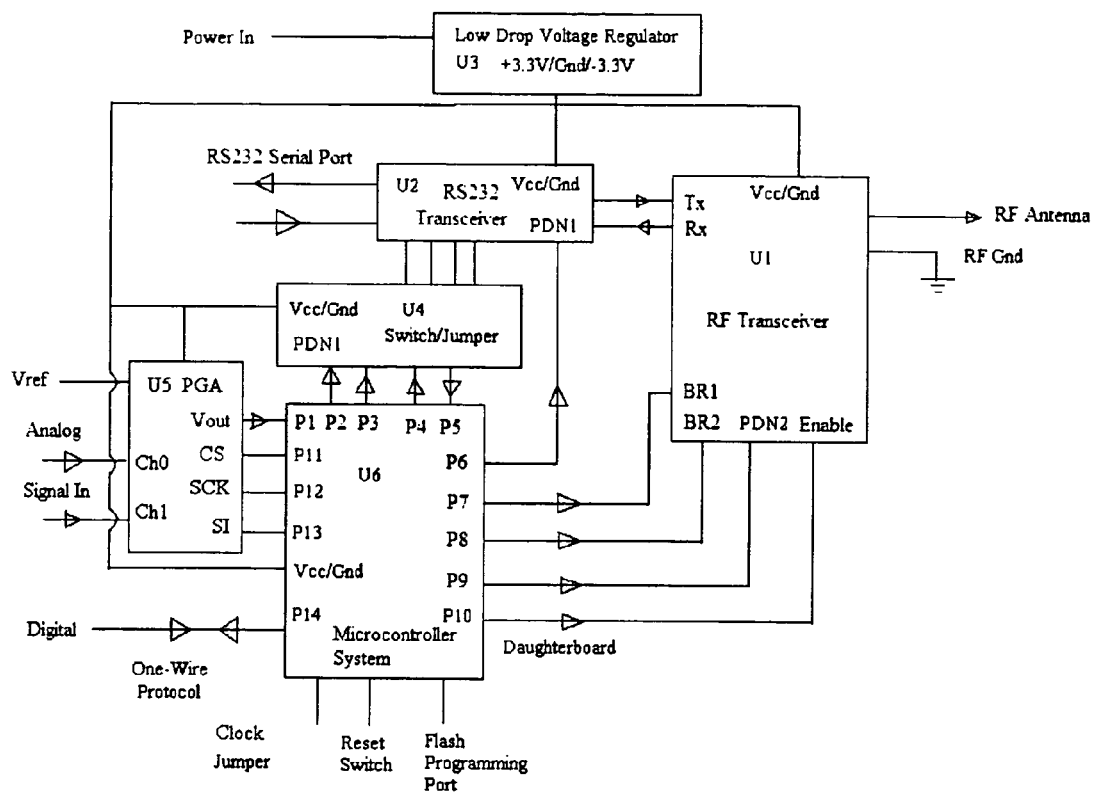
Figure 3. WEM motherboard internal block diagram

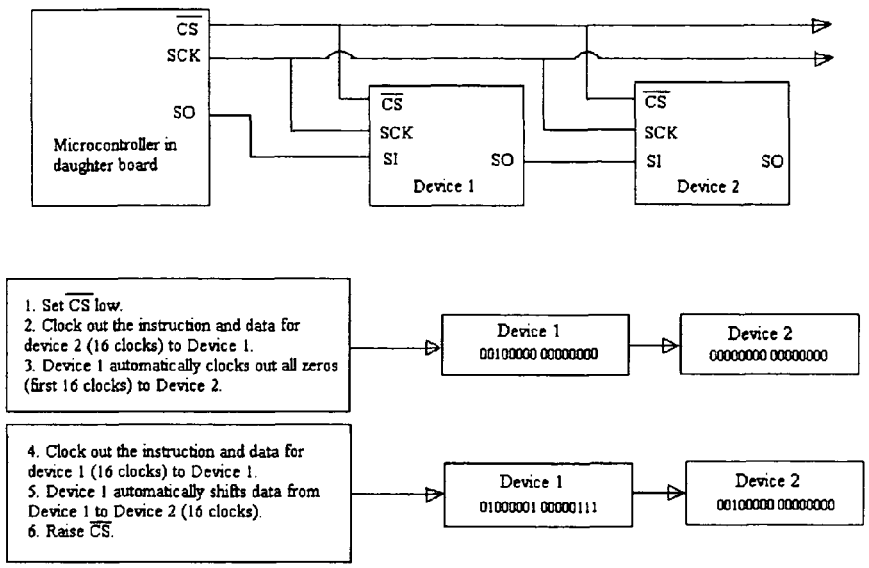
Figure 4. Daisy chain programmable gain amplifiers
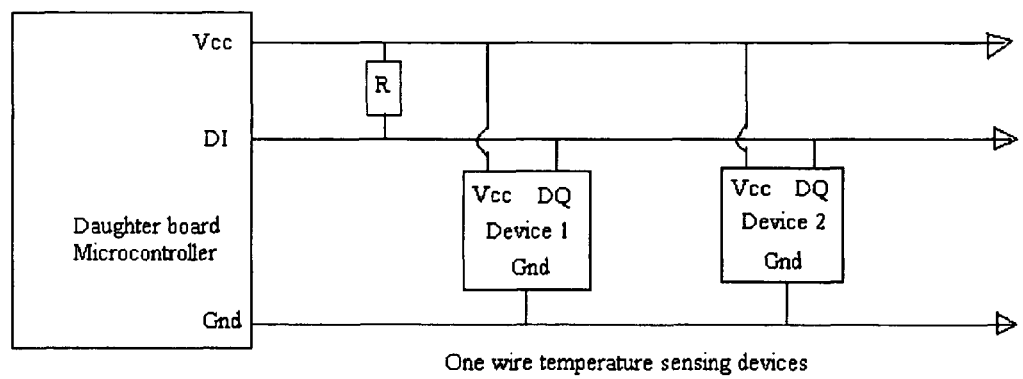
Figure 5. One-wire multi-drop or chaining of several temperature sensing devices.

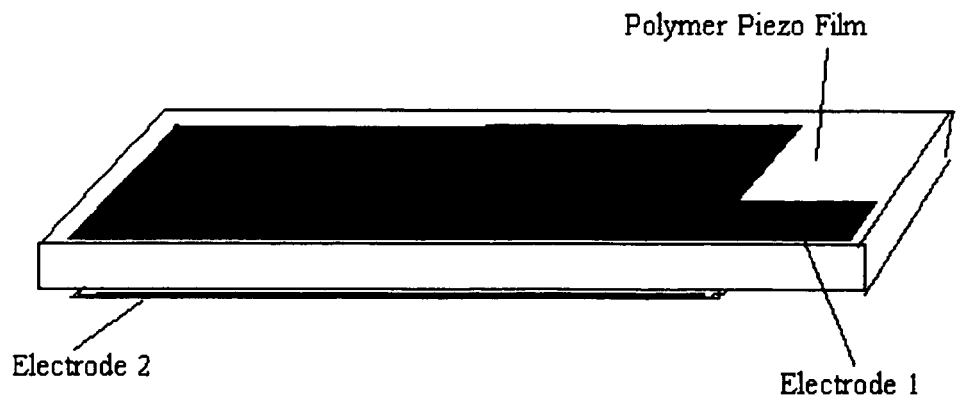
Figure 6. Acoustic Polymeric film with two electrodes printed with silver ink.
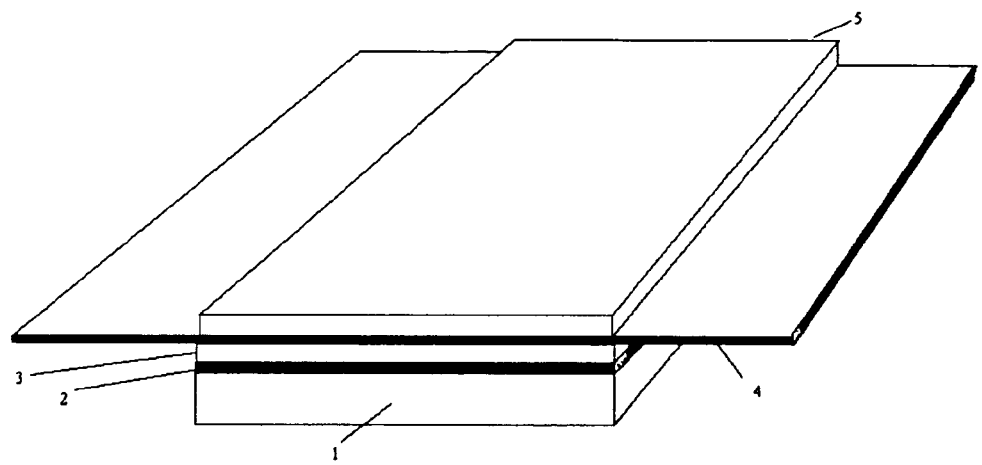
Figure 7. Acoustic Sensor with elastomeric support and flap
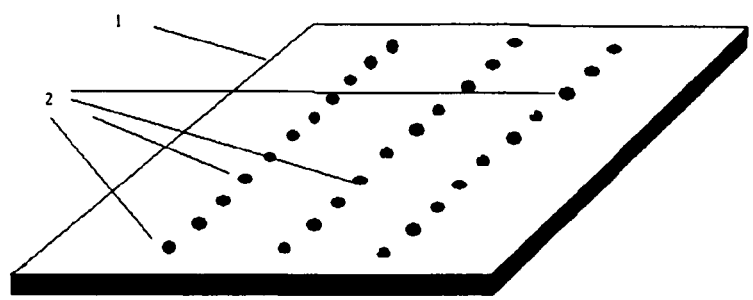
Figure 8. Holes in the acoustic sensor flap support for integrity

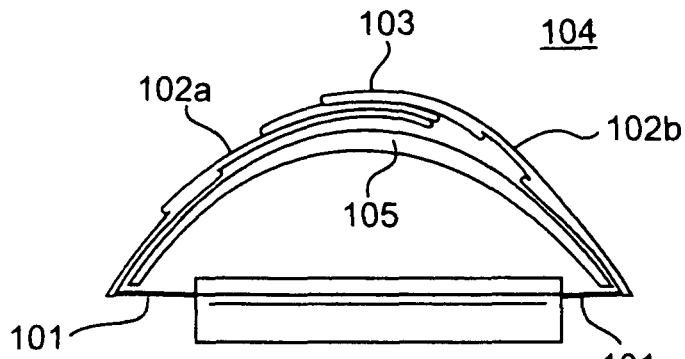

FIG. 9B

ACOUSTIC SENSOR ASSEMBLY WITH SENSOR AND SILICONE OR URETHANE IN RIGID HOUSING UNDER COMPRESSION IN CONTACT AND FIT CONTOUR OF THE HUMAN CHEST

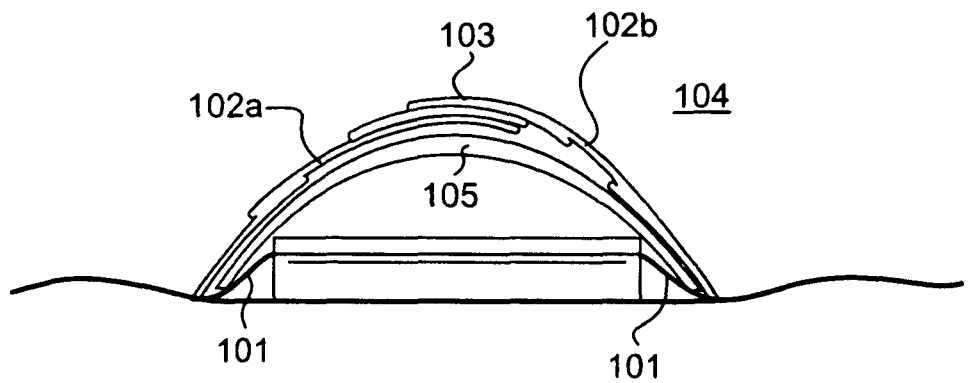

FIG. 9C

- —— CHEST BODY UNDER CONTACT
- —— EMBEDDED PIEZOELECTRIC FILM SENSOR
- —— ENERCHABLE ELASTIC (HIGHLY ELASTIC)
- —— VELCRO
- ▭ URETHANE ENCAPSULATING THE FILM SENSOR
- —— NON-STRETCHABLE FABRIC
- ◠ RIGID PLASTIC MOLD
- —— STITCHED TOGETHER A STRETCHABLE FABRIC TO A NON-STRETCHABLE FABRIC

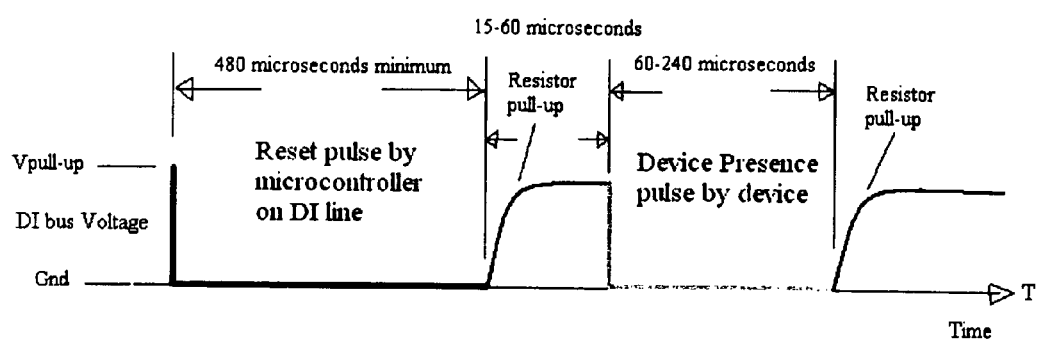
Figure 10. One-wire DI bus Reset and Presence pulse

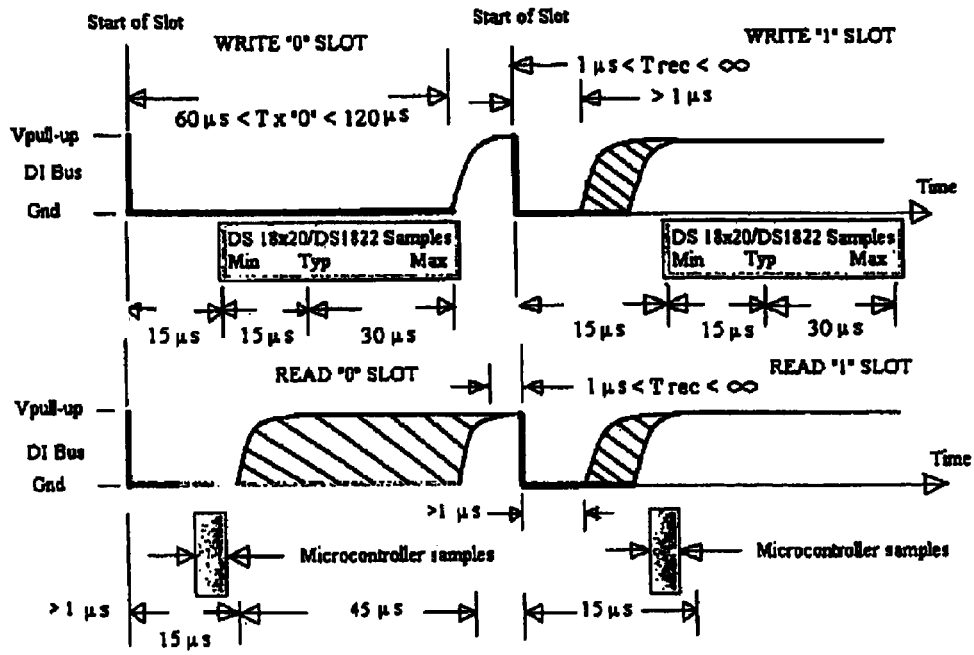
Figure 11. Write and Read Time Slots for the One-Wire Body Temperature Devices
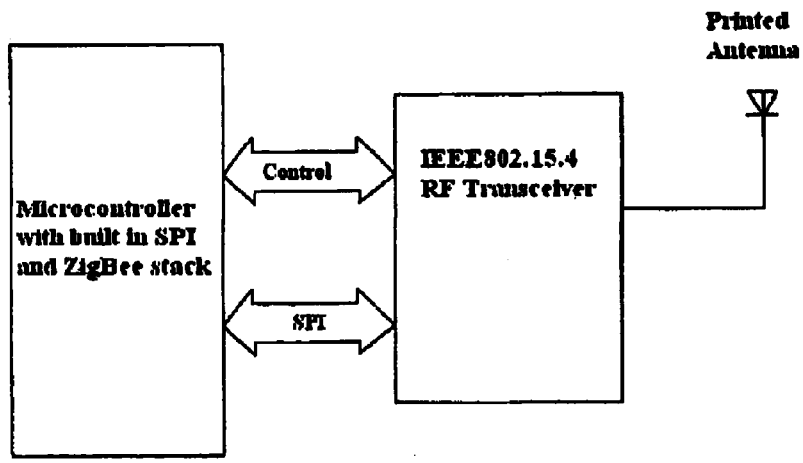
Figure 12a. ZigBee hardware setup between microcontroller and the RF transceiver.

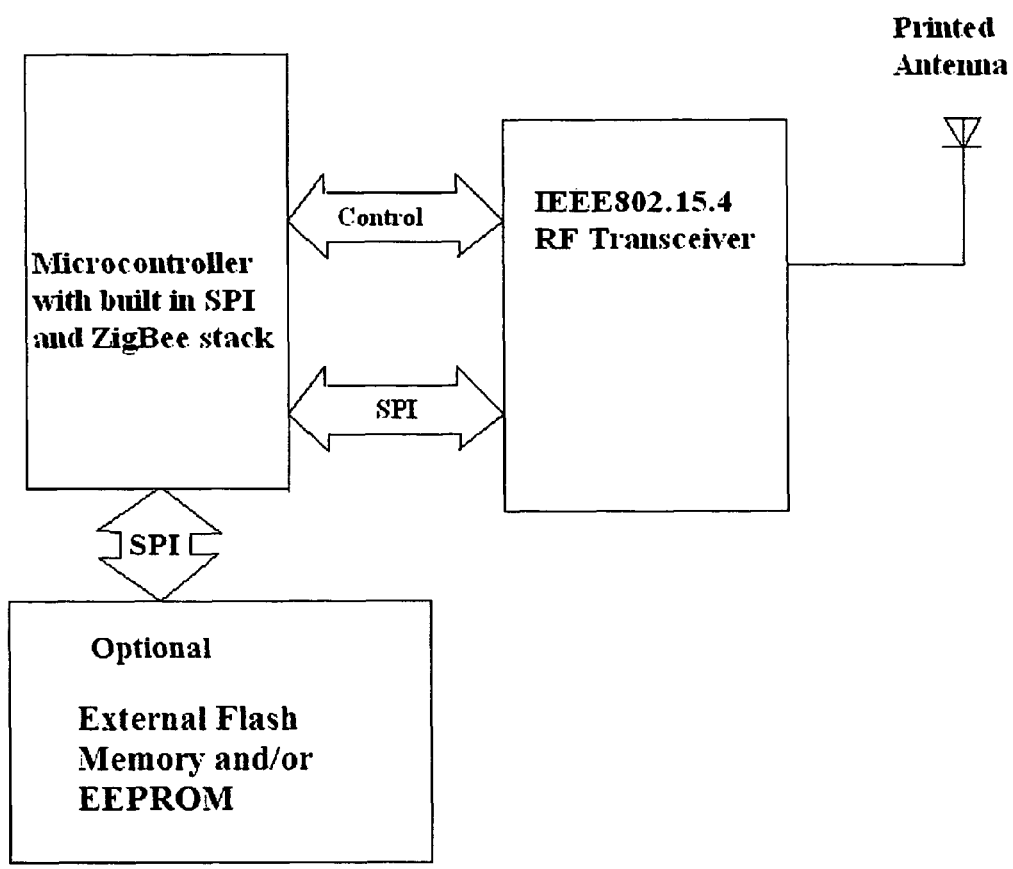
Figure 12b   An modified Zigbee solution with External flash memory and/or EEPROM device

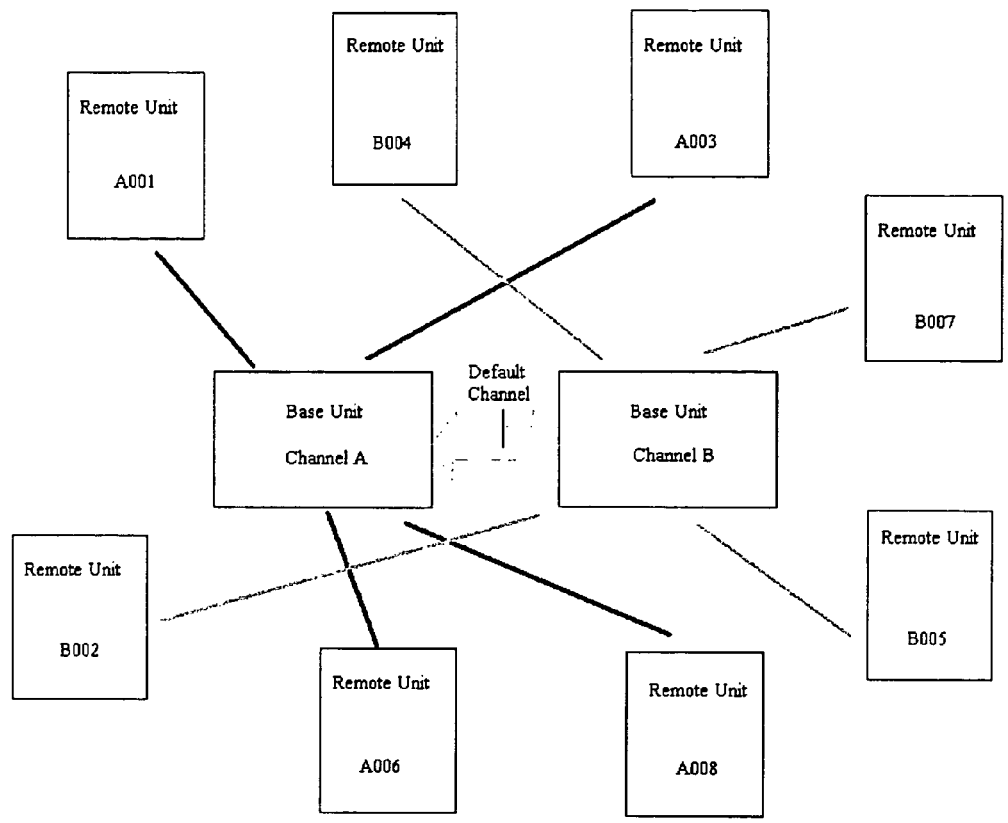
Figure 13. Remote and Base Units communication network

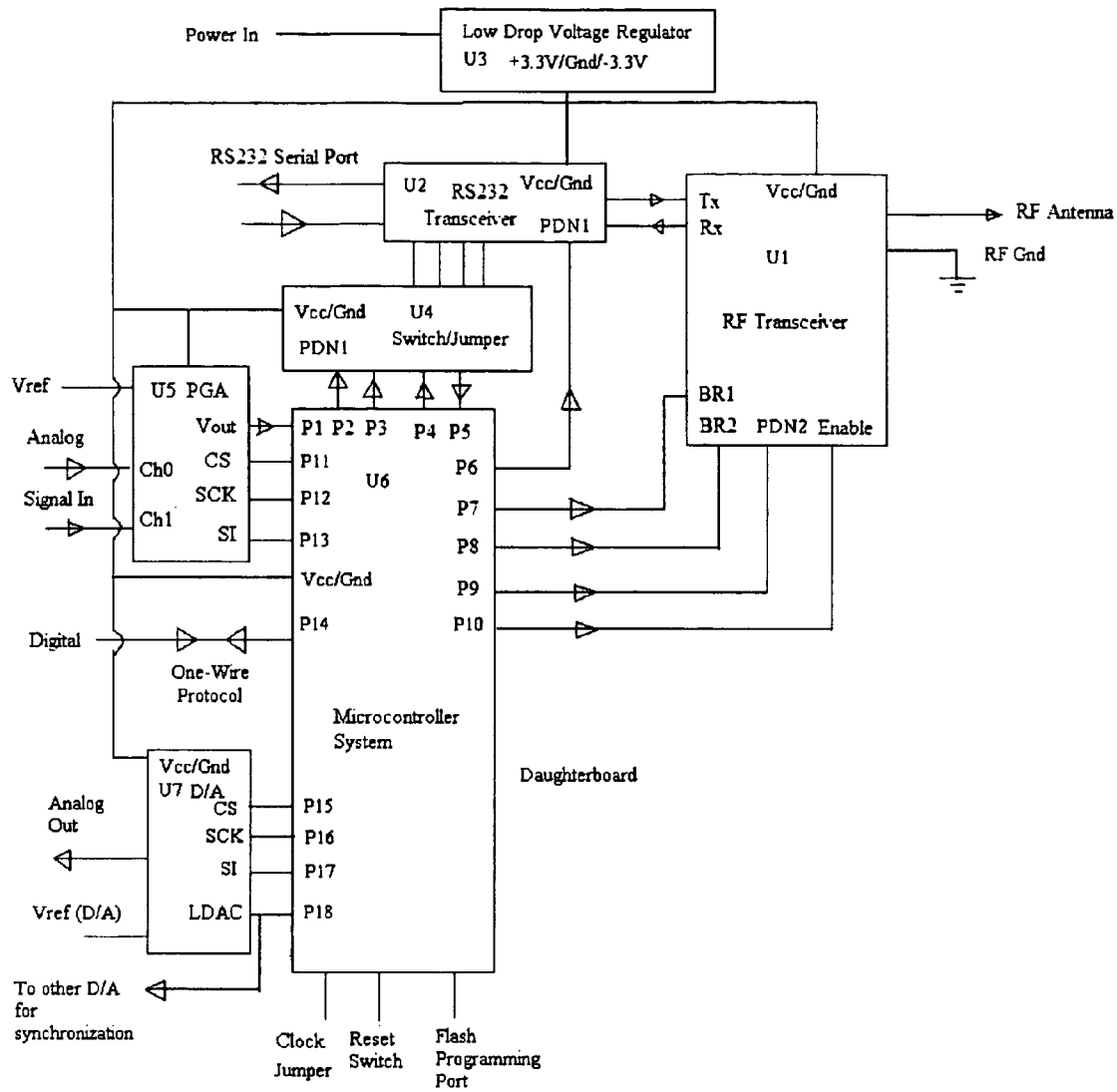
Figure 14. System with Analog voltage out modification to motherboard Figure 17. An example of a Fast Fourier Transform results of a human heartbeat waveform

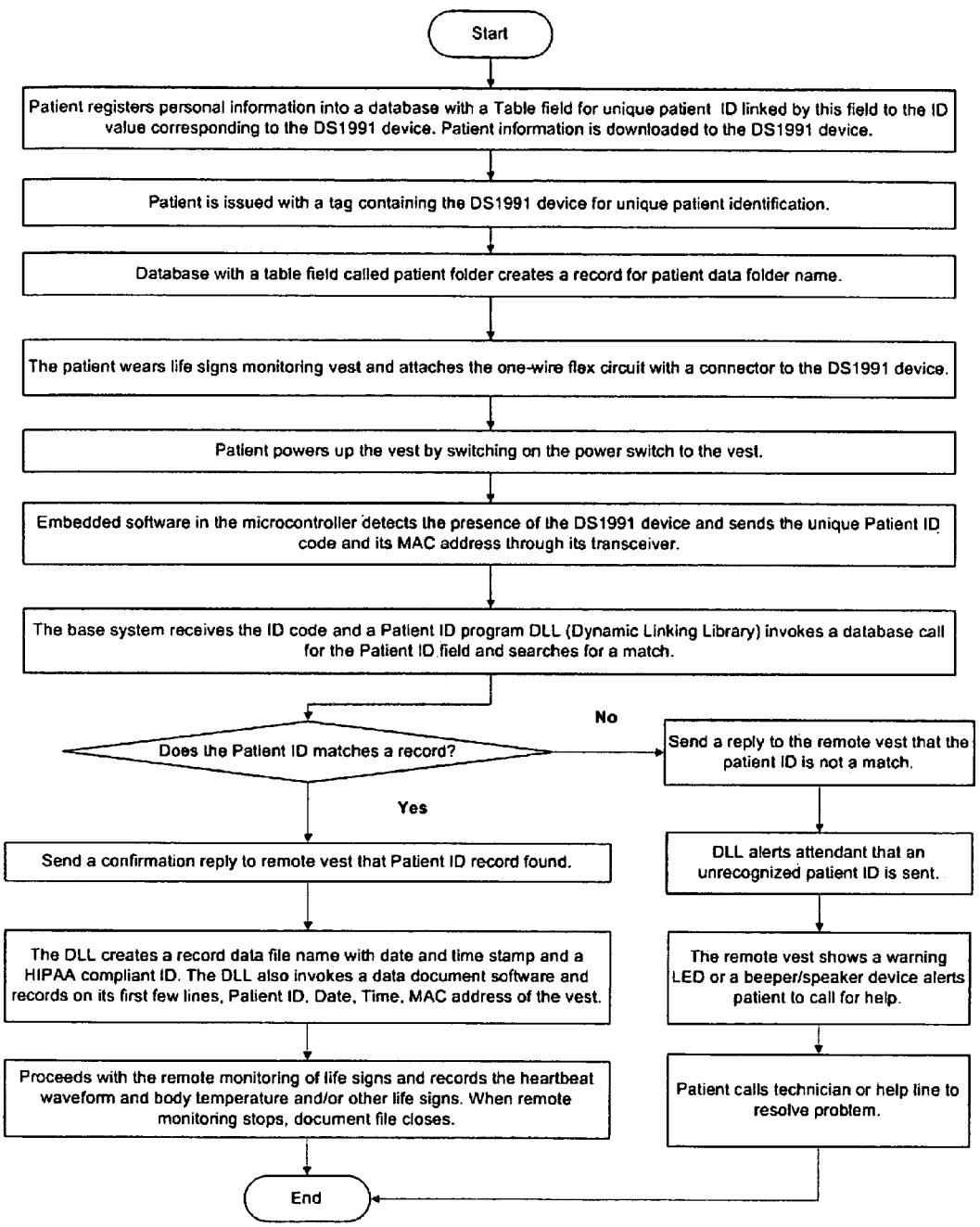
Figure 19. A flowchart showing process of automatic patient ID identification recognition and a secure database data collection.

SYSTEM AND METHOD FOR ACTIVE MONITORING AND DIAGNOSTICS OF LIFE SIGNS USING HEARTBEAT WAVEFORM AND BODY TEMPERATURE REMOTELY GIVING THE USER FREEDOM TO MOVE WITHIN ITS VICINITY WITHOUT WIRES ATTACHMENT, GEL, OR ADHESIVES

The present patent application is based on Provisional Application No. 60/718,723, filed Sep. 21, 2005, the entire contents of which are hereby incorporated by reference in their entirety.

BACKGROUND OF THE INVENTION

1. Field of the Invention

This invention relates to the general method of portable monitors and diagnostic systems for life signs in living beings or operating efficiency in a dynamic system. The ability to detect life signs such as live heartbeat waveforms and body temperatures relates to the physical health of a living being. In an emergency situation where people are trapped or are residing in their homes, this ability to determine their life signs can translate into vital information to make decisions for rescuing people.

2. Discussion of the Background

On the other hand, the vibration and temperature measurements in many dynamic systems can determine the health or reliability of the system. Such systems include motorized systems, engines, or even manufacturing equipment.

Vibrations produced by a beating heart generate heart sounds that, when detected by a stethoscope, can be electronically recorded by a phonocardiogram. The use of acoustic sensors permits the capture of the entire vibration spectrum. A vibration spectrum is a measurement of vibrating signal amplitude versus time. All vibration spectra can be transformed either in frequency or wavelet domains to improve the characterization of system dynamics, which can be correlated to actual physical phenomena, such as the closing of the heart values, the reverberation of the blood against the walls of the arteries, the valves in the veins, and the ventricular walls. When the vibrations of the vessels or ventricles come into contact with the chest wall, these vibrations can be detected as acoustic waves.

It is known that the phonocardiogram can be used to identify abnormal heart conditions, such as aortic stenosis, mitral regurgitation, aortic regurgitation, mitral stenosis, and patent ductus arteriosus. The transformed spectra give rise to unique peaks or pattern of peaks, allowing for quantifiable identifications and rules of computation to be performed.

The temperature of a person is very critical, especially in cold climates. The ability to correlate the person's heart rate against the body temperature gives a fuller picture of the severity of the situation.

This can be argued equally in the case of a vibrating system with motors, gears, bearings—it is known where the vibration frequency spectrum is characterized by many aspects of the system, including the motor rotation speed, the number of stators, and the bearings. Any changes in the vibration spectrum and temperature can suggest abnormality or premature failure.

In several occasions, it is necessary to have multiple channels for acoustic and temperature measurements; thus, the system requires an architecture that supports input expandability. A bidirectional wireless transmission capability allows the user to have freedom of movement for daily activities. The corresponding base unit can be in its vicinity. However, it would be too bulky for a field operation, so a field commander can wear a portable base unit in a pouch on the belt or pocket to become a relay station for an established network of existing communications. The existing network of communication can be in the form of Ethernet, USB, Internet, wireless IEEE802.11a/b/g or wireless IEEE802.16, etc. The network communication allows all the data to be stored, monitored, and further analyzed remotely. Since this is live data, monitoring the health and diagnostics in the field by experts in real-time becomes a reality.

SUMMARY OF THE INVENTION

In the prior art section, one of the following methods is used in the acoustic type of sensor design:
 a) gel,
 b) adhesive,
 c) fluid,
 d) air,
 e) cavity,
 f) membrane,
 g) bonding sensor material to a structure,
 where it is used for attachment to the user's body. When an adhesive is used to mount the sensor to the body, it can be quite a task to retrieve the sensor and realign the position of the sensor if it is placed wrongly and often not reusable. Furthermore, the use of gel is messy.

Acoustic sensors are particularly superior in providing a wide range of frequencies from sub Hertz to tenths of kilohertz. This edge has certain advantages over EKG or pulse oximetry IR sensors for the purpose of physiological process monitoring and diagnostics purposes.

Piezoelectric film materials are used in many acoustic sensors. These thin films are very delicate, non-elastic, but highly sensitive. The challenge to incorporate it in sensor design has always been its support and the coupling efficiency of the acoustic waves from the source to its film in generating electrical signals. The tearing of the film would be minimized when the force on its sides are equal; circular geometries are therefore preferred. When a film is bonded onto the edge of a hollow circular structure forming a diaphragm, the structure imposes a circular boundary condition restricting the kind of acoustic wave modes. Such structures would favor circular modes and diminish non-circular modes, similar to that for a drum. Since the heart's geometry and its associated pumping action are mainly non-circular, the acoustic signal efficiency is poor. The signal is further reduced when the coupling of acoustic waves to its surface is poor.

This invention uses an elongated piezoelectric film and embeds it within a silicone material with a shore-hardness in the range of 00-30 and 00-40 (where 00 refers to a Shore 00 hardness scale) to overcome these two shortcomings. Furthermore, the length of the film is aligned to the axis of the heart to pick up the longitudinal wave modes. The silicone material also matches the impedance. A piece of non-stretchable woven fabric is also embedded into the silicone as shown in FIGS. 6 and 7. The fabric has two roles. It supports the entire film and the silicone and it provides an orthogonal surface pressure for the silicone to be firmly pressed onto the chest with or without a thin undershirt. These sensors can therefore be Velcro attached or embedded to a well-fitted undershirt or even a brazier. The placement of sensors on the chest instead of hands or fingers will allow the user to perform daily activities with their hands or even during exercises. Oximetry sensors cannot be used on the chest. On the other hand acoustic sensors can be used on the arm wrists and also the neck for detection of heart pulses.

Another property of acoustic piezoelectric film sensors is the large variation in signal amplitudes, not found in EKG and oximetry sensors. EKG electrodes rely primarily on electrical contact, thus output voltages are usually in the order of millivolts. The designs for EKG monitoring systems are inadequate for handling acoustic sensing devices, since their digital signal resolution over a wide amplitude range is poor. The present invention overcomes this limitation with a programmable gain amplifier (PGA) on its front end. This amplifier ensures the maximum signal amplitude is presented across the analog to digital converter for maximum digital resolution. In addition, the architecture to support the PGA is based on the serial peripheral interface (SPI) bus; multiple acoustic sensors can be attached as shown in FIG. 3.

On the other hand, oximetry measurements require both infrared LEDs and detectors for heartbeat measurements. Intensity feedback-adjusted power-controlled LEDs provide the optimized detector with compensation to the detection average signal voltage, improving its signal to noise ratio. The present architecture also supports this kind of sensor as the feedback is through a digital to analog converter (D/A) with the SPI bus. These sensors are suitable for finger mounting.

This architecture also supports user communication with base unit selectivity. The base unit has the ability to select among remote systems. This is important in identifying and selecting the remote unit to allow the usage of two or more units in the same vicinity. This selectivity is based on two identifiers, a channel code and a user identification code, which are illustrated in FIG. 13. The channel code is the hardware allocation and the user ID is the software allocation. When the remote unit has the same channel as its base unit, both are periodically active waiting for instructions from the base unit. Only when the base unit sends a matching ID will it respond with a transfer of data. Different base units with different channels can operate at the same time without interference. At any single moment within its RF signal range, it is possible to communicate with the maximum number of separate channels less one for the base unit can have. There will always be one default channel. The base unit will always start on the default channel before switching to a free channel. The default channel is reserved for communications setup between remote units and base stations. This is a very flexible architecture.

BRIEF DESCRIPTION OF THE DRAWINGS

FIG. 1. Architecture of the Life Sign Active Monitoring and Diagnostic System

FIG. 2. The WEM unit with motherboard and daughter board and the various connectors FIG. 3. WEM motherboard internal block diagram FIG. 4. Daisy chain programmable gain amplifiers FIG. 5. One-wire multi-drop or chaining of several temperature sensing devices.

FIG. 6. Acoustic Polymeric film with two electrodes printed with silver ink.

FIG. 7. Acoustic Sensor with elastomeric support and flap

FIG. 8. Holes in the acoustic sensor flap support for integrity

FIG. 9B, 9C. FIGS. 9B and 9C illustrates a cross section of the assembly of FIG. 9A. FIG. 9A illustrates the sensor assembly before contacting body and FIG. 9B illustrates the sensor assembly after contacting body.

FIG. 10. One-wire DI bus Reset and Presence pulse

FIG. 11. Write and Read Time Slots for the One-Wire Body Temperature Devices

FIG. 12a. ZigBee hardware setup between microcontroller and the RF transceiver.

FIG. 12b. An modified Zigbee solution with External flash memory and/or EEPROM device FIG. 13. Remote and Base Units communication network FIG. 14. System with Analog voltage out modification to motherboard FIG. 15. Position alignment of acoustic heart beat sensor to the physiology of a person FIG. 16. Actual Acoustic heartbeat sensor measurement.

FIG. 19. A flowchart showing process of automatic patient ID identification recognition and a secure database data collection.

DETAILED DESCRIPTION OF THE PREFERRED EMBODIMENTS

Figure 9A:
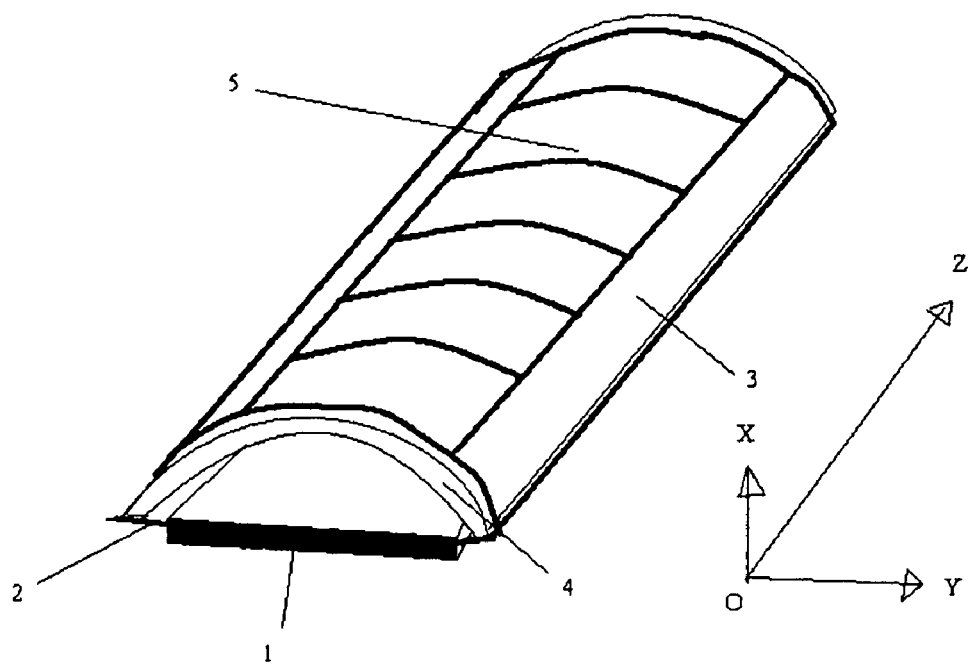
FIG. 9A. Semicircular rigid support for the acoustic sensor with its flap wraps around the curvature.

This detailed description of the preferred embodiments serves as a guideline on how it can be implemented in a preferred manner. It illustrates the concept and does not limit the scope of the invention. However, the organization, operation, advantages and objects of the invention can be more fully appreciated from the following description.

1) System Components

This invention involves the use of certain block elements, and FIG. 1 summarizes their relationship:
 a) Wearable Electronic Module (WEM) powered by its battery supply or through its communications port
 b) Analog Sensor/s (Acoustic)
 c) Digital Sensor/s (Body Temperature)
 d) Embedded Antenna (Flexible Printed Antenna)
 e) Wireless Network, Wireless Channels, Computer System
 f) Waveform and Spectra Analysis The core of the system is the WEM unit, which is shown as the blocks within the dotted box in FIG. 1. The design is based on nanoWatt technology and active components such as microcontrollers; transceivers have standby and/or power down modes to extend battery life. This is a multifunctional module that can be used in different methods for several locations in a large-scale system. The basic functionality of each of its ports is described below, and the ways it can be deployed in different roles in the overall system is described in the next section.

The motherboard of this module has two types of ports, Analog and Digital. The Analog port, represented by the letter 'A', receives analog signals and also provides power to the analog device such as an acoustic sensor and samples the data on demand. On the other hand, the digital port and Digital input data, represented by the letter 'D', provides digital communication protocols, such as the 'One Wire' standard, to its digital devices, such as body temperature sensors. The One-Wire protocol is used to reduce the number of data lines occupied by the sensor network.

This motherboard has a bidirectional serial communication port, allowing it to connect directly to the serial RS232 port or a USB port of a computer. The bidirectional communication capability permits it to receive instructions and to send data to the computer. In the USB configuration, it is even possible to draw power from the computer, eliminating the requirement of a battery pack.

The flexibility of this motherboard stems from the use of both jumpers and switches to reconfigure its hardware interface with the RF transceiver and the serial communication transceivers. On the other hand the daughterboard allows interface with motherboard for software programming.

Each WEM has RF transceivers on board, so communication with another WEM is possible. This allows the WEM to communicate with the remote computer system.

2) Wearable Electronic Module (WEM)

The WEM is an electronic module that performs the following functions (See FIG. 2):

a) Data acquisition—Input data acquisition in real time comes in two forms, analog and digital. Analog data acquisition is sent first to a front-end programmable gain amplifier (PGA), U5 as shown in FIG. 3. The digital data acquisition is performed using a one-wire protocol. This protocol reduces the number of interface lines to two with an optional third line for power.

In particular, we are referring to the acoustic sensor as the analog sensor and the body temperature sensor as the digital sensor.

b) Analog signal acquisition—The analog data acquisition may use of four lines to interface with the microcontroller—a voltage output line and three Serial Peripheral Interface (SPI) lines apart from the two positive and negative power supply lines. An optional external voltage reference line is used if the reference voltage is chosen to be a variable. Otherwise a fixed reference voltage is assigned.

The analog sensor output is connected to one of the two selectable channels of the PGA. The PGA is a selectable gain to its single-ended, rail-to-rail input/output operational amplifier. This gain selection allows the actual sensor signal dynamic range to be captured within its maximum bit resolution achieved by the analog to digital input port, U6-P1. A PGA example is Microchip PGA series MCP6S91/2/3. This chip controls its gain through three SPI interface lines, namely, SPI Chip Select (CS), SPI Clock Input (SCK), and SPI Serial Data Input. These interface lines are connected to U6-P11, U6-P12 and U6-P13 respectively on the microcontroller side.

The chip, MCP6S92, has two analog channels selected by an internal MUX and therefore up to two analog sensors can be used. If more analog sensors are needed, the data acquisition design can be expanded by daisy chaining the MCP6S93 as shown in FIG. 4 with each additional chip with two more sensors input. In contrast to MCP6S92, MCP6S93 has an additional SPI interface line, SPI serial Data Output, SO. The SO interface line is connected to the second device in line MCP6S93 SI interface line.

The digital resolution for most microcontrollers is either 10 bits or 12 bits. At a maximum of 3.3 volts, a 10-bit resolution gives approximately a +/−3.3 mV error. Therefore it is preferred to keep the input voltage presented to the A/D converter close to this maximum voltage to give a good resolution. This is the primary PGA function.

Sampling Rate:

Sampling rate is important for accuracy of capturing the waveform. According to the Nyquist criteria, the sampling frequency must be at least twice the frequency of the highest signal frequency component. For example, if the sampling time were 50 milliseconds, which is 20 Hz, then the highest frequency component captured would be 10 Hz. A normal person's heart rate is 60 beats per minute or one beat per second. Thus, a 20 Hz sampling rate is sufficient for a human heartbeat. However, for diagnostic purposes, much higher frequencies may be preferred, and this means sampling times should decrease. This sampling rate also affects the baud rate chosen if live data is to be collected.

c) Digital signal acquisition—The digital acquisition using the one-wire protocol uses only a data line (DI) and ground. Depending on the digital device it interfaces, a positive power line (VCC) may be required. The DI line from the digital sensor is connected to a digital signal pin input, U6-P14 on the microcontroller.

Another advantage of the one wire protocol is to have a chain on the number of digital temperature sensors on the same DI line as shown in FIG. 5. Each sensor has a unique identification code (ID). The DI line is connected to the DQ pin of each device. It first identifies the identification code and then activates the sensor to be active. Then the sensor reports its value to the ID.

The one-wire protocol is bidirectional and the device pin actually floats to give high impedance so that the active device controls the DI line. It is this property that provides the multi-drop or "chaining" capability to hundreds of devices on a single DI line. However, the one-wire signaling scheme is preferred for all its communications. This signaling scheme is described in more detail in the body temperature device section.

A one-wire device such device may be a Maxim DS1991 in a microcan package, which contains a guaranteed unique 48 bit factory set serial number with 1,152 bit read/write non-volatile memory. This provides the patient or user with a guaranteed unique patient identification tag, and this device stays permanently with the patient. When the vest is put onto the user, a flexible circuit with two conductors (conductive thread, or conductive printed thick film) is then connected to the DI line and ground line of the microcan (DS1991) as one of the one-wire devices shown in FIG. 5 (with microcan top being the I/O line and Gnd the bottom part of the microcan). This unique ID will be retrieved by the one-wire measurement protocol whenever life signs data. This retrieved unique ID will in turn direct the storage of the data record into the specific patient file folder in the database avoiding error in the data collection record process. This process flowchart is shown in FIG. 19.

d) Daughter board (microcontroller system with unique ID)—The use of the daughter board with all the microcontroller functions and clock on board is a flexible design. This allows the other portion of the board essentially unchanged while the daughter board can be programmed, upgraded or changed.

On the other hand, the architecture is flexible as it can that can be programmed from a daughter board which controls the data sampling rate and sequence on demand from its source via either its direct serial RS232 communication port or via the bidirectional RF transceiver port. It responds to the request by relaying the requested data back to its source with a preset baud rate.

The daughter board contains a microcontroller, a crystal clock or a resonator and an EEPROM. The EEPROM can be used to store a unique identification code. This code is used for identifying which daughterboard is used and its functionality. A good solution is to use the flash programmable Microchip microcontroller, PIC18F4550 (44QFN) or PIC18F2550 (SOIC-28), which has the USB2.0 communication protocol capability (12 Mbps) with 1024 bytes of USB buffer and internal 8 MHz oscillator. In addition, it has EUSART capability for the RS232 communication with both line transceivers and RF transceivers. The fast USB communication is for direct connection with the computer. The SPI communication capability is used for controlling the SPI interfaced PGAs. This microcontroller is ideal for the high-end performance of WEM, where it has to communicate with multiple WEMs. Furthermore, it has 36 I/O pins, 32768 bytes of program memory, 2048 bytes of RAM and 256 bytes of EEPROM memory and capable of supporting 48 MHz clock. This high clock speed and memory is necessary for both USB and the many tasks it has to perform.

Microchip microcontrollers, PIC16F688S/L or PIC16F690S/L are candidates for this application, operating at 3.3V common to U1 and U2, U4 and U5. The PIC16F688S/L comes in SOIC-14 package has 12 I/O and 8 A/D channels. On the other hand, PIC16F690S/L comes in SOIC-20 package, has up to 18 I/O lines and 12 channels 10-bit A/D. Both have EUSART for RS232 protocol, 4096 words of program memory, 256 bytes SRAM and 256 bytes of EEPROM. In FIG. 3, the daughter board includes 13 digital I/O ports and one A/D port giving a total 14 Pins. In addition, there are Vcc Pin and Gnd Pin, Reset and Programming shares one Pin (MCLR/Vpp), Clock In Pin and Clock Out Pin.

Since PIC16F688S/L has only 14 pins total, it still can be used if physical jumpers were to be used instead of electronic switching which eliminates four pins, P2 to P5. In addition Pin P10 can be eliminated by replacing it with a permanent enable line to U1. The jumper implementation has been demonstrated that the PIC16F688S/L microcontroller has adequate functions to perform the basic functions.

Although these two microcontrollers do not have hardware SPI built in function ports, software driven SPI communications are common, and they rely on the simulated clock with all the edges defined and synchronized. Alternatively, simple operational amplifiers such as National Semiconductor, LMC6036, can replace the SPI driven PGA with different feedback resistors shunted by CMOS transistors for gain selection.

Both chips have an internal 8 MHz clock. Should it be used instead of an external clock source, both Clock In and Clock Out will not be occupied, freeing two I/O lines.

Other manufacturers' microcontrollers can also be used as the preceding only illustrates the design requirements.

Switch/Jumper block—The basic function of the Switch/jumper block is to achieve the following communications:
  i) U1-Tx and U1-Rx to select its bidirectional communication with U2-Tx and U2-Rx. This enables the RF transceiver to communicate directly with the computer connected to the RS232 serial port.
  ii) U6-P4 and U6-P5 to select its bidirectional communication with the U1-Rx and U1-Tx of the RF Transceiver, U1. This is use in the remote unit in communication with a system connected to a computer.
  iii) U6-P4 and U6-P5 to select its bi-directional communication with the wired RS232 Serial Port, U2-Tx and U2-Rx. This is for the microcontroller communicating with the computer.
  iv) Idle state without Communication and the system is powered down.
    The control lines on the daughterboard, U6-P2 and U6-P3 control the communication used in switch/jumper, U4. This simply allows the switches/jumpers hardware to reconfigure the source of communication to its destination. In the case of jumpers, six lines are used instead of four.
  Cases i) and ii) are the two most basic communication modes and therefore can even be implemented with the use of physical switches or jumpers. However, for flexibility, electronic switching is preferred.

e) Serial Communications—The WEM serial communications functionality allows the WEM to communicate with the computer system, communicate with other WEMs in a direct line serial mode or a remote RF communication. The various serial communications mode are USB, direct line RS232 and RF communication. The USB to computer communication is already discussed in section d.

f) Direct line Serial Communication—The direct serial communication block allows the WEM to communicate bi-directionally with a computer system. It uses the Maxim chip, Max3225EEAP RS232 Transceiver, which has two sets of transmit and receive transceivers with an auto shutdown capability. This chip is ideal for U2 in the block diagram as shown in FIG. 3. The chipset can achieve a baud rate up to 1 Mbps and it has its internal dual charge pump using only a single voltage supply. However, the baud rate is normally limited by the baud rate achieved by the daughter board. In this case, it can communicate from 19200 baud to 115 kbaud. It is recommended that the system should not go lower than the 19200 baud rate.

g) Remote RF Serial Communication—The Abacom AT-XTR-903-A9 RF Transceiver chip operates in the carrier frequency range from 902-928 MHz does not interfere with the IEEE802.11g 2.4 GHz wireless network devices is ideal in such an environment. Furthermore, it has 169 selectable operating channels and three selectable input serial data speed (9600, 19200, 38400 bits/sec) via U6-P7 and U6-P8. U6-P9 control line can power down this chip to reduce power consumption. At 9600 baud, it performs both Hamming and Manchester encoding. At 19200 baud rate, it performs only Manchester coding. Finally at 38400 baud, it performs Scrambling. The highest level of data integrity is at 9600 baud, which allows correction of any single error occurring in any data nibble.

Channel selection is carried out by sending specific AT commands to the U1-Tx input. Channel "0" is the default channel. First the chip has to enter into command mode before the AT commands can be issued. These commands either read or write to its 16 available registers. After the correct command is issued, it can assign a certain frequency of operation. These register values can be saved into the EEPROM memory, which will not be lost when module is powered down. Once an exit command is issued the chip returns to its normal operation and data can be transmitted.

In power down state it switches all active circuitry consuming only ~10 µA of current through the use of the U2-PDN2 pin.

In addition, this chip provides Received Strength Signal Indicator (RSSI) with its value ranging from 0 through 9 where "0" is minimum field strength and "9" is maximum field strength.

h) Digital to Analog—In some measurements such as oximetry, additional analog control is needed. An example is driving the infrared LEDs and detectors for heartbeat measurements. This allows a feedback to adjust voltage to controlled LED intensity to optimized average signal voltage from the detector, thereby improving its signal to noise ratio. Microchip MCP4921/2 are digital to analog converters (D/A) with the SPI bus controls and they can be used as U7 as shown in FIG. 14. The I/O pins 15, 16 and 17 are SPI bus controls, allowing the microcontroller to send digital codes to set up the analog voltage. MCP4922 itself has two D/As. If more than two D/As are required, then I/O pin P18 is used for driving the LDAC signal pin, which synchronizes when the serial settings are latched into the DAC's output. Additional chip select is required and an I/O pin P19 (not shown) will be used.

i) Voltage Regulation—The WEM is supported by battery and it also indirectly provides power to the sensors. In the system illustrated here, 3.3 volts is used. Therefore, 3.3V Low Drop Voltage regulators are used to regulate the power supply to the chips U1, U2, U4, U5 and U6. The 3.3V Texas Instruments LDO chip TLV2217-33KTPR is used for U3.

j) Spectrum Analysis—The data obtained by the computer through the base unit will allow a time domain waveform to be plotted. Spectral analysis of this waveform requires either Fast Fourier Transform or Wavelet Transform performed on them.

3) Acoustic Sensors

The Acoustic sensor is able to pick up acoustic waves from the heart vibration. This sensor is based on an acoustic sensing film made of PVDF. The film produces a voltage and is captured on the two silver electrodes printed on the opposite faces of the polarized homopolymer of vinylidene fluoride PVDF material as shown in FIG. 6. These electrodes are riveted to a wire or conductive epoxy attached to the sensor connector. The film is given the freedom to flex.

The film itself is too sensitive and is enclosed in an elastomeric material, such as silicone or urethane plastic, which comes in the form of two parts liquid, A and B. By mixing part B to part A in a mold, an elastomeric structure in the form of the mold is created. It is recommended to use a shore hardness silicone or urethane in the range 00-30 to 00-40, which is soft like the flesh. At this range, the acoustic impedance between the flesh and the urethane or silicone is matched. This will reduce acoustic reflection and allows the acoustic waves to travel to the film sensor without much energy loss. This softness also allows the sensor to contour the curvature of the chest to leave no air gaps.

There are several steps to this molding of urethane plastic, which is shown in FIG. 7. First a thick layer of the urethane is created on a rectangular mold as layer 1. Layer 1 slab thickness preferably is greater than layer 3 slab thickness. Then before the curing of the plastic is complete, the film sensor is placed within centered within the flat surface. Then another layer of silicone or urethane plastic is poured. This time it is to bind the film sensor tightly to the mold. Let this second mold layer cure. Before the curing is complete, place the sensor flap sheet made of a highly flexible but non stretchable fabric, 4, with the holes as shown in FIG. 8 on the curing silicone or urethane and prevent air bubbles from being trapped. These holes allow the next layer of silicone or urethane pour to bind well to the layer of silicone urethane below the flap. This fourth layer labeled 5 completes the acoustic sensor structure.

The acoustic sensor needs a perpendicular pressure against the body for it to pick up the heartbeat waveform from the chest. This is achieved with a semicircular structure shown in FIG. 9. The pressure is to be applied in the X direction. The Y-Z axes define the plane in which the sensor is to rest on the chest or skin. The flap wraps around the semi circular surface and joined by an elastic sheet. The flap has a freedom to slide on this semi circular surface. Therefore the pressure on the film in the x direction is ensured when the pressure is applied to the chest in the negative x direction. This architectural design also eliminates the vibrations in the Y-Z plane.

FIGS. 9B and 9C illustrates a cross section of the assembly shown in perspective in FIG. 9A. Item 104 illustrates the sensor assembly of FIG. 7. As shown in FIG. 7, the sensor assembly includes stretches of fabric 101 that extend beyond the periphery of the polymer. Additional pieces of elastic material 102a, 102b are sewn to or otherwise attached to the fabric extensions 101. The elastic material wraps around curved rigid member 105 (also shown as item 4 of FIG. 9A) to a region of overlap 103. The pieces of elastic material 102a, 102b are fastened together at region of overlap 103 by sewing, Velcro™ or other means.

Figure 15:
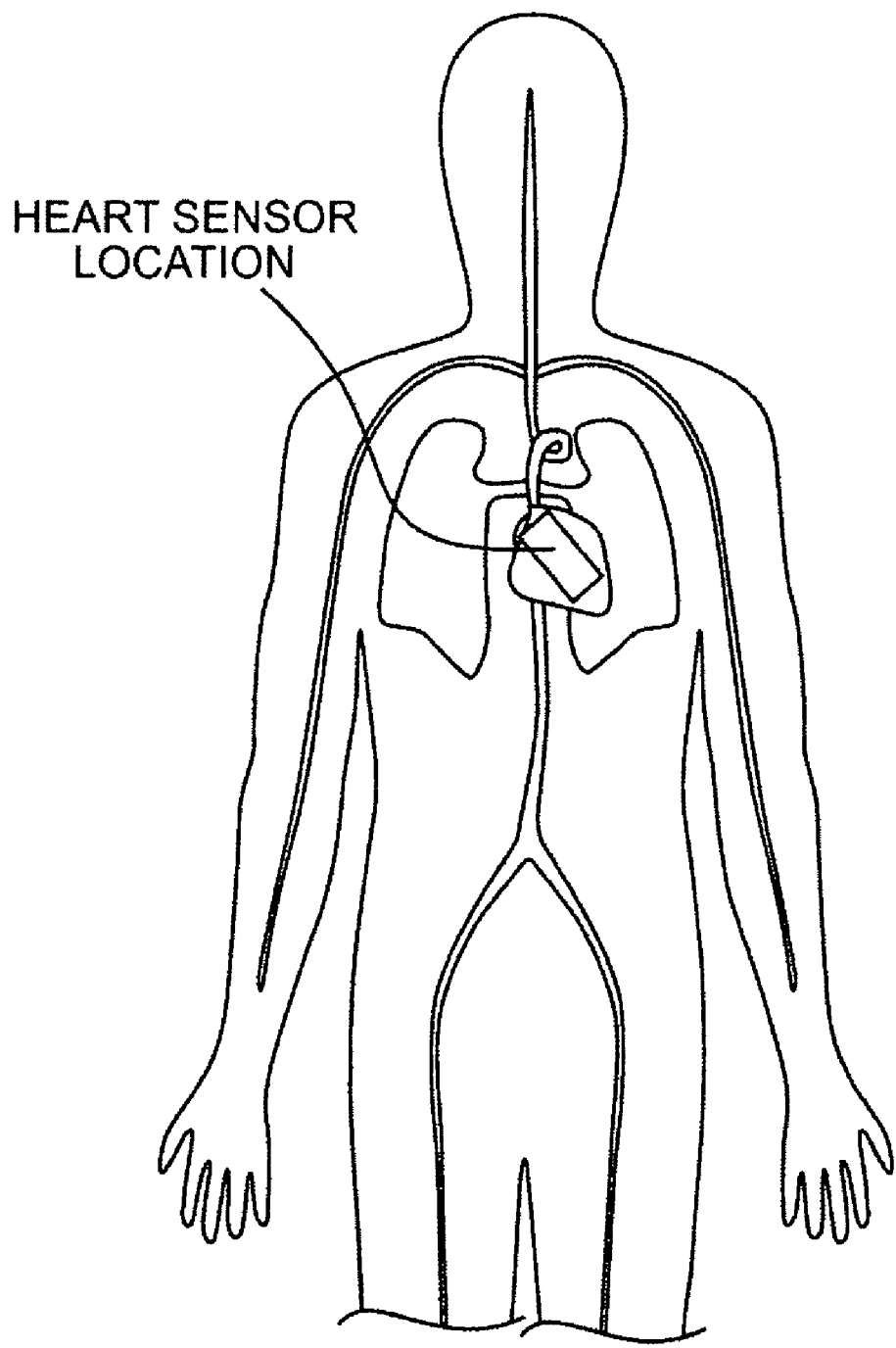
Figure 16:
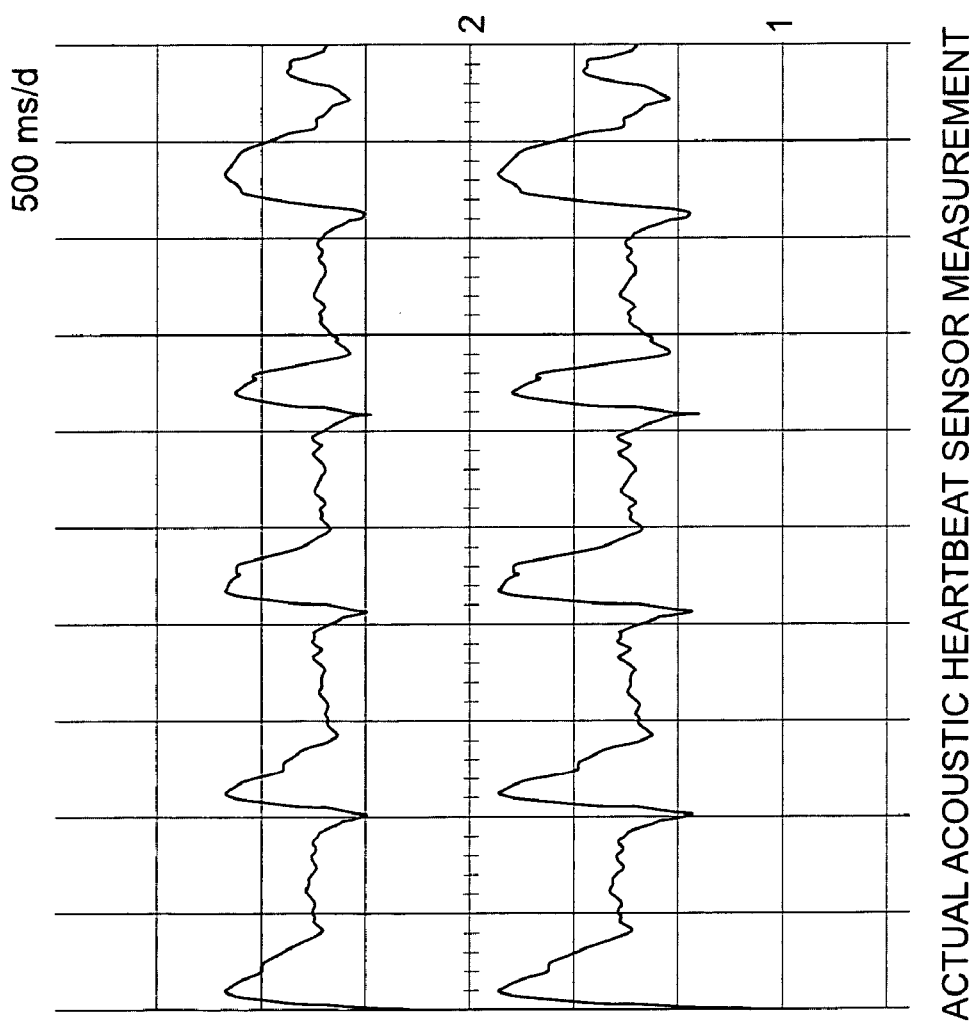

The alignment in placing the sensor is shown in FIG. 15. A typical acoustic sensor heart beat waveform measured is shown in FIG. 16. The corresponding vagal tone can be extracted from the heartbeat waveform data.

It should be noted that this technology can be applied to other parts of the body just as effectively or better. Arm wrists and neck are particularly good places for detecting heartbeat waveforms too. The sensor can be applied to the abdomen of pregnant women to detect fetus heartbeat waveform and also its vagal tone.

4) Body Temperature Sensor—This sensor is a one-wire protocol sensor. This sensor can be from a family of temperature sensors such as Maxim DS18S20, DS18B20, DS1822, and DS2422. These are on-wire protocol devices, which can be chained together as shown in FIG. 5. Each of these devices has an identification code, which allows the data received on the DI bus being distinguished.

The following is a description how each of these devices communicates with the microcontroller through the DI bus. It is recommended for the clock on the Microchip microcontroller be set at a minimum of 8 MHz since it takes 4 clock cycles per instruction. All communications are achieved through the use of "Time slots", which allow data to be transmitted over the DI line. Therefore it is preferred that the microcontroller I/O port connected to the DI bus have three digital states, namely, "high", "low" and "float". The "float" state occurs when the microcontroller I/O port transform into a high impedance state, which allows the devices on the DI bus to control the line. Each communication cycle begins with a reset pulse initiated by the microcontroller pulling low on the DI line for a minimum of 480 microseconds as shown in FIG. 10. At the end of the reset pulse the DI line is pulled up high for duration between 15 and 60 microseconds by the pull-up resistor, R, shown in FIG. 5. A device presence pulse signified by pulling low the DI line by the device with duration between 60 and 240 microseconds after reset.

Both writing and reading to the device requires the use of a write and time slots respectively as shown in FIG. 11. In writing, the microcontroller pulls DI bus from logic high (inactive) to logic low state. The write slots duration must stay be within 60 μs to 120 μs with a 1 ms minimum recovery time between cycles. The microcontroller pulls the DI bus low for the duration of the time slot during the write "0". However, for the write "1" time slot, the microcontroller first pulls the bus low and then releases the line within 15 μs after the start of the time slot.

In the case of reading the device by the microcontroller, a read time slot is first initiated by the microcontroller pulling the DI bus low for 1 μs then releases it so that the DS18x20/DS1822 device can take control of the DI bus, presenting the bus with valid data (high or low). Again all read time slots must stay within the 60 μs to 120 μs duration with a minimum 1 μs recovery time between cycles. The device has to respond within the read and write time slots for the data to be read or written.

The identification of the device begins with the typical initialization sequence of a Reset by the microcontroller. Then the slave devices respond by issuing simultaneous presence pulses. Since each slave device identification code is unique, the microcontroller issues the Search ROM command on the DI bus. This identification code can be used to identify the location of the sensor on the body. The following is the description of ROM search process.

i) Each device will respond to the Search ROM command by placing the value of the first bit of their respective ROM codes onto the DI bus. The microcontroller then read the bus value. When there is one or more devices with their first ROM code value "0", it will cause the bus to go pull low. Those devices with 1's for their first ROM code do not affect the bus if it was already pulled low by any one device, whose first ROM is a "0". This is because these can only draw current from the resistor, R, and pull down the bus voltage. This is essentially a logical AND operation for all devices on the bus. The microcontroller will read low if any of the first ROM code value is "0".

ii) All the devices on the DI bus will respond to this read by placing the complement of their first bit of their ROM codes onto the DI bus. The consequence of this action by those devices whose first ROM code is "0" and changing them to a "1" will allow the DI bus to stay high.

iii) At this time the microcontroller has to deselect those devices with ROM code "1" by pulling the DI bus low or equivalent to writing a value "0" on the DI bus. This action will allow only those devices with the first ROM code "0" to remain connected to the DI bus.

iv) The microcontroller performs a second ROM code from the devices. The devices with the second ROM code "0" will first pull the DI bus low and then switch to its complement value to allow the DI bus to stay high. Whereas those devices with the second ROM code "1" do not need to switch to its complement value. This means that each time the DI bus senses a switch from "0" to "1" change, there must be at least one device with a ROM code "0" for that code position. Again by pulling the DI low deselect those devices with second ROM code "1".

v) By the process of de selection, the microcontroller will finally able to select only one device and read its ROM code successfully.

vi) Then by repeating this process each of the devices on the DI bus will be identified.

vii) The microcontroller learns the unique ROM code of each device during each ROM search pass. The time required to learn one ROM code is:

$$960 \ \mu s + (8 + 3 \times 64) 61 \ \mu s = 13.16 \ ms$$

This means it can identify up to 75 devices on the same DI bus per second.

The reading of the temperature involves selecting the device by the Match ROM function first. This is achieved by sending a reset. If reset is true, return false. Then send a Match ROM command (0x55) followed by another send command with the ROM code. This will avoid data collisions with other devices on the same DI bus.

If this returns true then send reset followed by a write skip ROM command and then a start temperature conversion command. Next send another skip ROM command and then a Read Scratch Pad command. The temperature value is stored in the scratch pad.

5) Embedded Antenna (Flexible Printed Antenna)

Both remote unit and base unit use antennas for transmission. In the case of a 900 MHz transmission design, antennas can be part of the wearable fabric and a length approximately 16.5 cm or half its wavelength using the formula:

$$\text{Length } L = \lambda/2 = \text{Speed of Light, } c/(2 \times \text{Frequency of Transmission)} \quad (1)$$

The antennas tested were printed with conductive Polymer Thick Film (PTF) Ink first and then followed by a flexible insulating dielectric to cover the traces, except where the connections are on the non-stretchable woven fabric made of polyester or nylon. The PTF inks typically are cured at 125 degrees Celsius. Since the fabric is woven, the antenna is quite rugged, highly flexible, and soft to the touch. For the purpose of aesthetic value, the printed side can be on the inside. However, the body, with high water content, tends to be a ground plane. It is recommended to have another fabric material spaced between the antenna and the skin.

The antenna connection can be formed by using snapped on buttons directly snapped on to the cured conductive ink with conductive epoxy on button's back to secure it. Protective insulating coating should be applied to any exposed epoxy or conductive traces to prevent issues like silver migration when the antenna is in contact with water.

6) Wireless Network, Wireless Channels and Computer System

As mentioned earlier, this wireless network architecture supports users with a remote unit to communicate a base unit. It is the base unit that selects the channel the remote unit to operate in. A base unit has the ability to communicate with more than one remote unit. Each unit has a unique identification including the base unit. The base unit distinguishes itself from the remote unit from the daughter boards program and the switch or jumper setting. Once the unit is established remote or base, the overall system would be controlled by an external computer communicating with the base either through a USB, or RS232 serial port. If the base is connected to an embedded system that links USB to a wireless port for IEEE802.11a/b/g WiFi communication network; this computer can be in a remote location. An alternative is to incorporate the 802.11a/b/g universal wireless LAN chipset, Atheros AR5112. This increases the complexity, power consumption and cost on the unit. A simpler solution would be to use an embedded device could be achieved using GumStix's solution, which is based on the Intel PXA255 processor, roughly the processing speed of 233 MHz, AMD K6 processor.

In FIG. 13, multiple remote units and base units are in their own wireless network. It is important for the base unit to identify and select the correct remote unit, since there can be more than one remote unit within the wireless network range. This selectivity is based on two identifiers: a channel code and a user identification code. A channel code defines a physical channel such as "A" or "B", which can be two separate frequencies channels and therefore a hardware allocation. The user ID is on the other hand a software allocation and it is a code in the EEPROM.

The base unit will always start with the default channel and then look for a free channel to switch into. No two base units within the wireless range should have the same channel other than the start up period with the default channel. The base units will start with a receiver mode and scan for any base units. If there is a similar base unit it will inform which channel that unit is operating at. After the scan it will establish all base unit frequencies of operation. It will check also counter check with the database, which channels are used and which remote units are there.

When a new remote unit is introduced into the network, it will start to communicate with it at the default channel first to inform it which new channel it should switch to. After handshake is complete, both remote and base unit will change to the new channel. When the remote unit has the same channel as its base unit, it will stay periodically active waiting for instructions from the base unit. Only when the base unit sent the ID is identical to the remote unit, that unit will respond with a transfer of data.

The database of remote units accessed by a base unit can support several remote units on the same channel. This base unit will communicate with those units as well. Different base units with different channels can operate simultaneously without interference. At any single moment within its RF signal range, it is possible to communicate with one less than the maximum number of separate channels. There will always be one default channel reserved. During shutdown, all units return themselves to the default channel. This channel assignment process can be seen as dynamic. This is a very flexible architecture.

Other RF Protocols:

Another RF protocol available for this application is Zig-Bee, which operates at 20 kbps with transceivers frequency at 900 MHz to 250 kbps with transceivers frequency at 2.4 GHz. ZigBee supports the IEEE802.15.4 standard transceivers. The Zigbee technology allows thousands of devices (routers and end devices) to be connected in the network with unique MAC addresses and network addresses. This allows many vests to operate in the same vicinity. The Zigbee hardware setup uses a microcontroller with SPI bus and some control lines to the RF transceiver as shown in FIG. 12a. This is a fully acknowledged protocol and supports low latency devices and its range is between 30 and 300 feet. It can also operate in both secured and unsecured mode with an optional 128 bit AES encryption. An example of such a 2.4 GHz transceiver is Chipcon CC2420 in a 48 pin QLP package and it operates at 3.3V with 16 channels. Other examples of a 2.4 GHz transceiver chip is Ember EM250 and EM260. The EM250 is a single chip solution with both microcontroller and RF transceiver built in. There is limited code space available in its flash memory. A preferred solution is to use an EM260 where it replaces the RF transceiver, U1, as shown in FIG. 14, to add EEPROM or Flash memory devices to the SPI bus for buffer storage of real-time data prior to transmission, and to add program memory space as shown in FIG. 12b. The Chipcon chip CC2431 has a hardware solution for providing location based signal strength on triangulation with its routers' location. Such location tracking can provide mobile data on a moving patient while lifesigns are being monitored. A similar approach can be implemented on the EM250, EM260, Abacom AT-XTR-903-A9 (900 MHz) transceiver by using the RSSI (Receive Signal Strength Indicator) values as approximate distance measurements from the fixed or known location devices it communicates with. The EM250, EM260 and CC2431 RF transceivers are designed to coexist with other 2.4 GHz products running the EEEE802.11 protocols. For example, CC2420, uses the following input/output (I/O) connections to the microcontroller:

i) FIFO,
ii) FIFOP,
iii) CCA,
iv) SFD,
v) CSN,
vi) SPI Clock (SCK),
vi) Serial Data In (SI),
vii) Serial Data Out (SO),
viii) Reset,
ix) Vreg_en, There are other IEEE802.15.4 compliant RF transceivers that will operate at 915 MHz ISM with 40 kbps and 10 channels. The microcontroller, PIC18F4550, discussed in daughter's board section has 32 Mb memory, SPI bus and computational speed to run the ZigBee stack. Other possible wireless communication protocol is Bluetooth. The above examples show how the system can use the different protocols but not as a limitation.

7) Waveform and Spectra Analysis

The periodic sampling of the signal for the analog sensors such as acoustic sensor is a performed only for a given total number of samples. In the Fast Fourier Transform (FFT) algorithm, it is necessary to select a number of samples given by the formula:

$$\text{No of samples required} = 2\char`^n \qquad (2)$$

where ^ is to the power of,
n is an integer.

for a complete set of input required to perform the FFT.

256, 512 and 1024 samples are legitimate set of sample points. If the sampling rate is 50 milliseconds, they take 12.8, 25.6 and 51.2 seconds respectively to collect a full set. This is an acceptable time frame for a common application.

Figure 17:
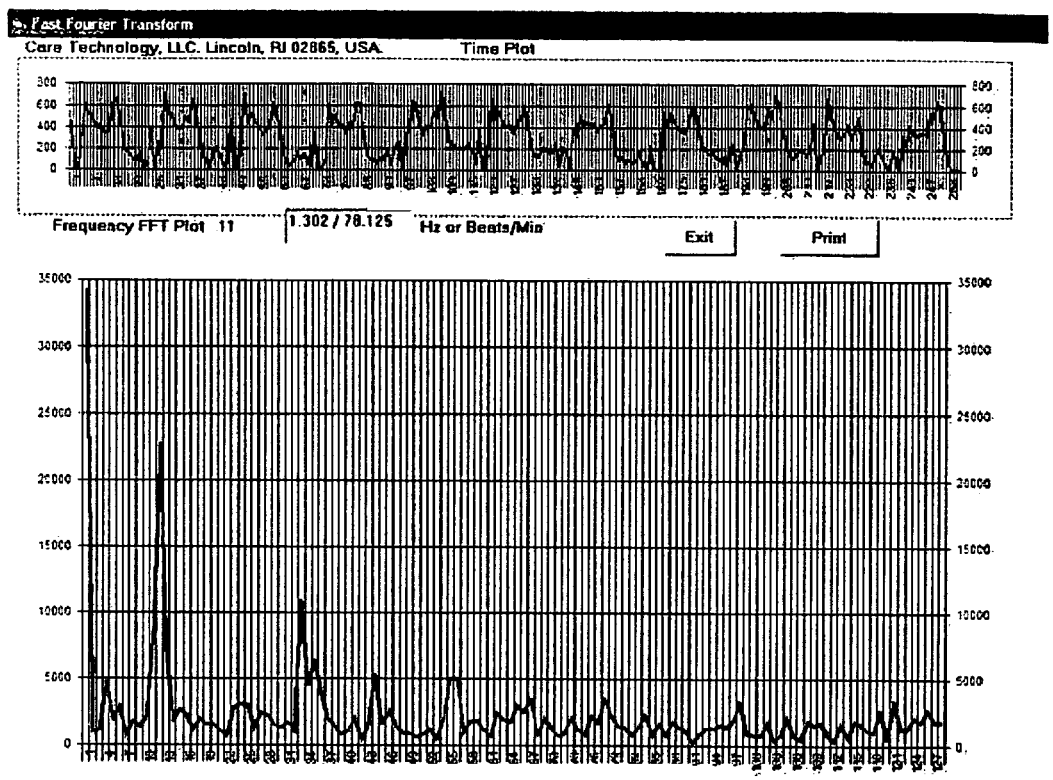
FIG. 17. An example of a Fast Fourier Transform results of a human heart waveform.
Figure 18:
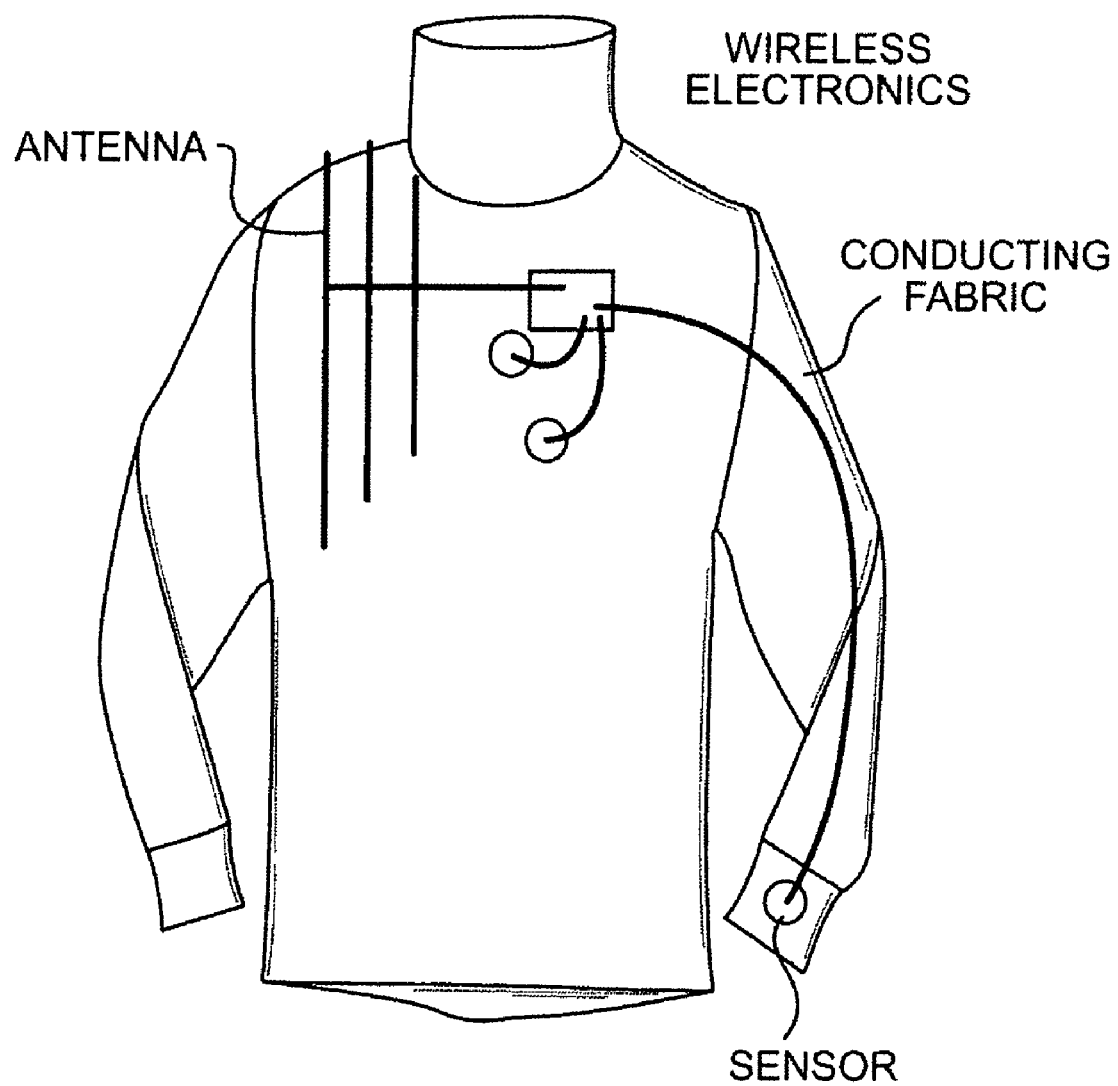
FIG. 18. An example of a wearable life signs monitoring and diagnostic vest featuring use of conducting fabric to integrate electronics to antenna, sensors and power sources.

The FFT gives a set of coefficients for each corresponding discrete frequency. FIG. 17 shows a plot of the human heart beat waveform in time domain (top trace) and a corresponding frequency domain (bottom trace). There are several noticeable peaks and the second peak from the left (corresponding to discrete frequency Number 11) is the regular dominant heart beat rate of 78. The largest peak at zero frequency is the dc level of the signal and can be eliminated. There are certain rules that can be used to detect the heart rate and the heartbeat waveform for diagnosis.

If a set of heart beat waveforms is documented as normal for a particular person, the relative FFT coefficients can be treated as a good reference. Relative coefficients would be the normalized set as shown in equation 3. This set should be collected for when the person is fully rested to under stress, like walking and running on a treadmill. An example would be to collect five sets of readings for each range of dominant heart beat rate. Assume there are ten sets on dominant heart rate. Each of the relative dynamic set of frequency coefficients, $F_r(m)$, is expressed as a function of a given heart beat rate, r.

$$\Sigma F_r(m) = 1 \qquad (3)$$

where m=n/2, numerically equals to half the value of sampling points.

A polynomial function, $\phi_m(r)$, is fitted that for each m value, it gives the interpolated value for the anticipated normalized $m^{th}$ Fourier coefficient for the heartbeat rate, r (shown in equation 4). This gives the pattern on how the normalized coefficients would change with the dominant heart beat rate, r. Notice that there is no case where r=0, since it means the heart is not beating and $r_{max}$ is probably no more than 200. Assume r1 is the minimum heart beat rate, and rk is the maximum heart beat rate, then $$\phi_m(r) = A(r)F_{r1}(m) + A(r)F_{r2}(m) \ldots + A(r)F_{rk}(m) \qquad (4)$$

This formulation will produce a known good set of waveform coefficients for the database on that particular subject.

When a new reading is taken on the same subject, it is now possible to use the actual readings and compare its new coefficients to that predicted by the equation (4) given the measured heart beat rate. If the sum of set of coefficients exceed a given percentage or any individual coefficient exceeds a given percentage, then it can be used for an alert.

Similarly, this can be performed for wavelet transform coefficients. Only the basis sets and functions are very different.

This is a methodology on how to analyze the heartbeat waveform for the purpose of monitoring and diagnostics.

The invention claimed is:

1. A wearable electronic apparatus comprising:
   a wearable garment;
   an acoustic sensor attached to the garment and positioned to sense an acoustic signal of a garment wearer, the acoustic sensor including:
      an elongated rectangular piezoelectric film for sensing the acoustic signal;
      electrodes attached to both planar surfaces of the piezoelectric film;
      an elastomeric material which covers the piezoelectric film and the electrodes; and
      a non-stretchable fabric attached to the elastomeric material for maintaining structural integrity of the acoustic sensor; and
   a wireless communication device transmitting acoustic data of the acoustic sensor of a wearer,
   wherein the elastomeric material has a shore-hardness in a range of about 30 to 40 on the Shore 00 hardness scale.

2. The device of claim 1 further including a one-wire device having a unique identification code.

3. The device of claim 2 wherein the wireless communication device transmits the unique identification code of the one-wire device.

4. The device of claim 1 further including a temperature sensor attached to the garment and sensing a temperature signal of a garment wearer.

5. The device of claim 4 wherein the wireless communication element further transmits temperature data.

6. The device of claim 4 wherein the temperature sensor is a one-wire device having a unique identification code.

7. The device of claim 6 wherein the wireless communication element further transmits the unique identification code of the temperature sensor.

8. The device of claim 1 wherein the garment is a wrist band.

9. The device of claim 1 wherein the wireless communication device transmits data in response to a received command.

10. The device of claim 1 wherein the acoustic signal is a vagal tone.

11. A life sign monitoring method comprising:
    placing on a body a garment having an acoustic sensor and a wireless communication device, the acoustic sensor comprising:
       an elongated rectangular piezoelectric film for sensing the acoustic signal;
       electrodes attached to both planar surfaces of the piezoelectric film;
       an elastomeric material which covers the piezoelectric film and the electrodes; and
       a non-stretchable fabric attached to the elastomeric material for maintaining structural integrity of the acoustic sensor;
    sensing a heartbeat acoustic signal of the body;
    generating acoustic data based on the sensing;
    transmitting acoustic data of the body,
    wherein the elastomeric material has a shore-hardness in a range of about 30 to 40 on the Shore 00 hardness scale.

12. The method of claim 11 wherein the garment includes a one-wire device having a unique identification code.

13. The method of claim 12 wherein the wireless communication device transmits the unique identification code of the one-wire device.

14. The method of claim 11 wherein the garment further includes a temperature sensor attached to the garment and sensing a temperature signal of a garment wearer.

15. The method of claim 14 wherein the wireless communication element further transmits temperature data.

16. The method of claim 14 wherein the temperature sensor is a one-wire device having a unique identification code.

17. The method of claim 16 wherein the wireless communication element further transmits the unique identification code of the temperature sensor.

18. The method of claim 11 wherein the garment is a wrist band.

19. The method of claim 11 wherein the wireless communication device transmits data in response to a received command.

20. The method of claim 11 wherein the acoustic signal is a vagal tone.

21. The apparatus of claim 1, wherein the non-stretchable fabric includes a plurality of holes.

22. A wearable electronic apparatus comprising:
    a wearable garment;
    an acoustic sensor attached to the garment and positioned to sense an acoustic signal of a garment wearer, the acoustic sensor including:
       an elongated rectangular piezoelectric film for sensing the acoustic signal;
       electrodes attached to both planar surfaces of the piezoelectric film;
       an elastomeric material which covers the piezoelectric film and the electrodes; and
       a non-stretchable fabric attached to the elastomeric material for maintaining structural integrity of the acoustic sensor; and
    a wireless communication device transmitting acoustic data of the acoustic sensor of a wearer,
    wherein the elastomeric material has a shore-hardness in a range of about 30 to 40 on the Shore 00 hardness scale; and
    wherein a long side of the piezoelectric film is aligned to an axis of a heart of the garment wearer for sensing longitudinal wave modes of the heart.

23. The apparatus of claim 1, wherein the garment is attached to limb muscles of the garment wearer.

24. The apparatus of claim 1, wherein the acoustic signal sensed through the acoustic sensor is analyzed with respect to a normalized signal representative of a normative state of the garment wearer.

25. The apparatus of claim 24, wherein the wireless communication device alerts a monitoring facility when the acoustic signal deviates from the normalized signal.

26. The apparatus of claim 1, wherein the acoustic signal is a measurement of a life sign critical to health of the garment wearer.

27. The method of claim 11, wherein the non-stretchable fabric includes a plurality of holes.

28. A life sign monitoring method comprising:
    placing on a body a garment having an acoustic sensor and a wireless communication device, the acoustic sensor comprising:
       an elongated rectangular piezoelectric film for sensing the acoustic signal;
       electrodes attached to both planar surfaces of the piezoelectric film;
       an elastomeric material which covers the piezoelectric film and the electrodes; and a non-stretchable fabric attached to the elastomeric material for maintaining structural integrity of the acoustic sensor;
sensing a heartbeat acoustic signal of the body;
generating acoustic data based on the sensing;
transmitting acoustic data of the body,
wherein the elastomeric material has a shore-hardness in a range of about 30 to 40 on the Shore 00 hardness scale; and
wherein a long side of the piezoelectric film is aligned to an axis of a heart of the garment wearer for sensing longitudinal wave modes of the heart.

29. The method of claim 11, wherein the garment is attached to limb muscles of a garment wearer.

30. The method of claim 11, further comprising analyzing the sensed acoustic signal with respect to a normalized signal representative of a normative state of a garment wearer.

31. The method of claim 30, wherein the acoustic data is transmitted to a monitoring facility when the acoustic signal deviates from the normalized signal.

32. The method of claim 11, wherein the acoustic signal is a measurement of a life sign critical to health of the garment wearer.

* * * * *